(12) United States Patent
Oths et al.

(10) Patent No.: US 11,910,724 B2
(45) Date of Patent: Feb. 20, 2024

(54) THICKENER SYSTEMS FOR ORAL CARE COMPOSITIONS AND A METHOD FOR PREPARING THE SAME

(71) Applicant: ISP INVESTMENTS LLC, Wilmington, DE (US)

(72) Inventors: Philip John Oths, Mendham, NJ (US); Shafiq Sahar Wahidi, Pomona, NY (US); Petros Gebreselassie, Whitehouse Station, NJ (US); Hani M. Fares, Somerset, NJ (US)

(73) Assignee: ISP INVESTMENTS LLC, Wilmington, DE (US)

( * ) Notice: Subject to any disclaimer, the term of this patent is extended or adjusted under 35 U.S.C. 154(b) by 0 days.

(21) Appl. No.: 16/763,068

(22) PCT Filed: Nov. 8, 2018

(86) PCT No.: PCT/US2018/059791
§ 371 (c)(1),
(2) Date: May 11, 2020

(87) PCT Pub. No.: WO2019/094568
PCT Pub. Date: May 16, 2019

(65) Prior Publication Data
US 2020/0306161 A1  Oct. 1, 2020

Related U.S. Application Data (60) Provisional application No. 62/584,574, filed on Nov. 10, 2017.

(51) Int. Cl.

| | | |
|---|---|---|
| *A61K 8/55* | (2006.01) | |
| *A61K 8/73* | (2006.01) | |
| *A61K 8/86* | (2006.01) | |
| *A61Q 11/00* | (2006.01) | |
| *A61K 8/34* | (2006.01) | |
| *H10N 50/85* | (2023.01) | |
| *G11C 11/16* | (2006.01) | |
| *G11C 11/15* | (2006.01) | |
| *H10B 61/00* | (2023.01) | |
| *H10N 50/10* | (2023.01) | |
| *H10N 50/01* | (2023.01) | |
| *H10N 50/80* | (2023.01) | |

(52) U.S. Cl.
CPC ............ *H10N 50/85* (2023.02); *A61K 8/55* (2013.01); *A61K 8/731* (2013.01); *A61K 8/86* (2013.01); *A61Q 11/00* (2013.01); *G11C 11/15* (2013.01); *G11C 11/161* (2013.01); *H10B 61/22* (2023.02); *A61K 8/345* (2013.01); *G11C 11/1659* (2013.01); *H10N 50/01* (2023.02); *H10N 50/10* (2023.02); *H10N 50/80* (2023.02)

(58) Field of Classification Search
CPC ....... A61Q 11/00; G11C 11/15; G11C 11/161; G11C 11/1659; H10N 50/01; H10N 50/80; H10N 50/10; H10N 50/85; A61K 8/86; A61K 8/55; A61K 8/731; A61K 8/345; H10B 61/22
See application file for complete search history.

(56) References Cited

U.S. PATENT DOCUMENTS

| | | | | |
|---|---|---|---|---|
| 4,992,259 A | * | 2/1991 | Schiraldi | A61K 8/733 424/49 |
| 5,004,597 A | * | 4/1991 | Majeti | A61K 8/21 424/464 |
| 5,192,529 A | | 3/1993 | Garlick et al. | |
| 5,521,234 A | | 5/1996 | Brown et al. | |
| 6,344,488 B1 | | 2/2002 | Chenite et al. | |
| 8,211,411 B2 | * | 7/2012 | Deckner | A61K 8/25 424/49 |
| 2008/0071077 A1 | | 3/2008 | Dijk et al. | |
| 2018/0221259 A1 | * | 8/2018 | Potanin | A61K 8/44 |

OTHER PUBLICATIONS

Referenced cited in the international search report of PCT Application No. PCT/US2018/59791 published on May 16, 2019 under publication No. WO2019/094568.

\* cited by examiner

Primary Examiner — Lezah Roberts
(74) Attorney, Agent, or Firm — William J. Davis; Nathalie Tietcheu (57) ABSTRACT

A substantially anhydrous thickener system in the form of a gel for use in oral care compositions comprising: carboxymethyl cellulose or its salts thereof, a chelating agent, and hydroxyethyl cellulose, in a solvent system, wherein the thickener system is heated to a temperature ranging from about 70° C. to about 120° C. to form the gel. A method of preparing the thickener system for use in oral care compositions comprises the steps of: a) charging a mixture of hydroxyethyl cellulose and carboxymethyl cellulose into a reaction container, b) dissolving the mixture of a) in a solvent system, c) charging a chelating agent into b), and d) heating the resultant of c) to a temperature of 70°-120° C. for at least about 10 minutes.

11 Claims, 2 Drawing Sheets

THICKENER SYSTEMS FOR ORAL CARE COMPOSITIONS AND A METHOD FOR PREPARING THE SAME

CROSS-REFERENCE TO RELATED APPLICATIONS

This application is a U.S. National Phase filing under 35 U.S.C. § 371 of international Application No. PCT/US2018/059791, filed November 8. 2018, and published as WO/2019 094568 on May 16. 2019, which claims benefit of priority U.S. Provisional Patent Application No. 62/584,574, filed Nov. 9, 2017. The entire contents of each of the prior applications are incorporated herein by reference in their entirety.

FIELD OF THE INVENTION

The present application relates to a thickener systems, and more particularly, to a substantially anhydrous thickener system(s), in the form of a gel, for use in oral care compositions, and a method of preparing the thickener system. Also, disclosed is an oral care composition comprising said thickener system.

BACKGROUND OF THE INVENTION

Oral care compositions are well known in the art. See, e.g., U.S. Pat. Nos. 5,288,480 and 6,723,304, the disclosures of which are hereby incorporated by reference in its entirety. Oral care compositions typically include an oral care ingredient and a thickening system. The thickening system(s) is used to develop the desired viscosity for the oral care compositions, and therefore, render the composition suitable for its intended use.

U.S. Pat. No. 4,022,881 discloses a dentifrice with a reduced tendency to lose rigidity and viscosity.

U.S. Pat. No. 4,426,373 discloses a dental cream of desirable rheological properties containing a gelling agent system comprising hydroxyethyl cellulose and sodium carboxymethyl cellulose in a weight ratio of about 3:2 to 2:3.

U.S. Pat. No. 5,192,529 discloses a low-stringiness and relatively non-weeping toothpaste compositions comprising: (i) a polyol, (ii) an abrasive, (iii) a thickener system comprising: (a) a low viscosity carboxymethyl cellulose gum having a viscosity ranging from about 50 to about 500 cps when 4% is placed in water at 25° C.; and (b) a low viscosity hydroxyethyl cellulose gum having a viscosity ranging from about 75 to about 200 cps when 5% is placed in water at 25° C., the amount of the carboxymethyl cellulose and hydroxyethyl cellulose being present in a weight ratio of about 5:1 to about 1:5, said toothpaste having good cohesion and sufficient shortness of texture so as not to become significantly stringier upon additional shear, and upon extrusion retains body without stringiness, slump, separation, shrinking, collapse or weeping.

U.S. Patent Publication No. 2006/0099154 A1 discloses a teeth whitening method comprising a person contacting her/his teeth with a teeth whitening composition for a teeth whitening time period, and then contacting said teeth with a teeth and/or gum desensitizing composition for a desensitizing time period and/or contacting said teeth with said desensitizing composition prior to contact with the whitening composition.

U.S. Patent Publication No. 2009/0269287 A1 discloses an oral care composition having improved dispersibility comprising (i) a thickening/binding agent, and (ii) an orally acceptable carrier.

Very low water toothpastes (e.g., those containing less than 10% w/w water) commonly have ingredients which are sensitive to water. While not totally anhydrous, the water activity/availability in these toothpaste compositions is further reduced by the humectants present, particularly glycerin, which further bind the water. Very low water-available thickener systems are useful in protecting water-labile ingredients such as stannous fluoride, stannous chloride and higher order polyphosphates such as sodium hexa-metaphosphate. Accordingly, it would be advantageous to have improved oral care compositions with a substantially anhydrous thickener system that protect the water-labile ingredients.

SUMMARY OF THE INVENTION

The primary objective of the present application relates to a substantially anhydrous thickener system for use in oral care compositions comprising: (i) carboxymethyl cellulose or its salts thereof, (ii) a chelating agent, and (iii) optionally hydroxyethyl cellulose, in a solvent system, wherein the thickener system is heated to a temperature ranging from about 70° C. to about 120° C. to form a gel.

Another objective of the present application relates to a substantially anhydrous thickener system in the form of a gel for use in oral care compositions comprising: (i) carboxymethyl cellulose or its salts thereof, (ii) a chelating agent, and (iii) a hydroxyethyl cellulose in a solvent system, wherein the thickener system is heated to a temperature ranging from about 70° C. to about 120° C. to form a gel.

Yet another objective of the present application relates to a substantially anhydrous thickener system in the form of a gel for use in oral care compositions comprising: (i) carboxymethyl cellulose or its salts thereof, (ii) disodium pyrophosphate and (iii) hydroxyethyl cellulose in a solvent system comprising a mixture of water, glycerin, propylene glycol, and polyethylene glycol, wherein the thickener system is heated to a temperature ranging from about 70° C. to about 120° C. to form the gel.

Still one more objective of the present application relates to a substantially anhydrous thickener system for use in oral care compositions comprising: (i) a mixture comprising from about 0.1% to about 10% w/w of carboxymethyl cellulose or its salts thereof and hydroxyethyl cellulose, (ii) disodium pyrophosphate in an amount from about 0.01% to about 2% w/w, and a solvent system in an amount from about 50% to about 90% w/w of a mixture of water, glycerin, propylene glycol, and polyethylene glycol, wherein the thickener system is heated to a temperature ranging from about 70° C. to about 120° C. to form a gel.

One more objective of the present application relates to a method of preparing the thickener system for use in oral care compositions comprising the steps of: (a) charging carboxymethyl cellulose or its salts thereof into a reaction container; (b) dissolving the mixture of (a) in a solvent system; (c) charging a chelating agent into (b); and (d) heating the resultant of (c) to a temperature of 80° C. for at least about 10 minutes.

Another objective of the present application relates to a method of preparing the thickener system for use in oral care compositions comprising the steps of: (a) charging a mixture of carboxymethyl cellulose or its salts thereof and hydroxyethyl cellulose into a reaction container; (b) dissolving the mixture of (a) in a solvent system, (c) charging a chelating agent into (b); and (d) heating the resultant of (c) to a temperature of 80° C. for at least about 10 minutes.

One more objective the present application relates to an oral care composition comprising (i) a substantially anhydrous thickener system comprising: carboxymethyl cellulose or its salts thereof, a chelating agent, and optionally hydroxyethyl cellulose, in a solvent system, wherein the thickener system is heated to a temperature ranging from about 70° C. to about 120° C. to form a gel; and (ii) one or more orally acceptable additives.

Another objective of the present application is to provide an oral care composition comprising: (i) from about 50 to about 90% w/w of a substantially anhydrous thickener system comprising: carboxymethyl cellulose or its salts thereof, a chelating agent, and hydroxyethyl cellulose, in a solvent system, wherein the thickener system is heated to a temperature ranging from about 70° C. to about 120° C. to form a gel; and (ii) from about 10 to about 50% w/w of one or more orally acceptable additive.

BRIEF DESCRIPTION OF THE DRAWINGS

Further embodiments of the present invention can be understood with reference to the appended figures.

DETAILED DESCRIPTION OF THE INVENTION

While this specification concludes with claims particularly pointing out and distinctly claiming that which is regarded as the invention it is anticipated that the invention can be more readily understood through reading the following detailed description of the invention and study of the included examples.

As used herein, the following terms, unless otherwise indicated, have the meanings set out below.

All publications, articles, papers, patents, patent publications, and other references cited herein are hereby incorporated herein by reference for all purposes to the extent consistent with the disclosure herein.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof", "and combinations thereof", and "combinations thereof" as used herein refers to all permutations and combinations of the listed items preceding the term.

All percentages, parts, proportions and ratios as used herein, are by weight of the total composition, unless otherwise specified. All such weights as they pertain to listed ingredients are based on the active level and, therefore, do not include solvents or by-products that can be included in commercially available materials, unless otherwise specified.

All references to singular characteristics or limitations of the present application shall include the corresponding plural characteristic or limitation, and vice-versa, unless otherwise specified or clearly implied to the contrary by the context in which the reference is made.

Numerical ranges as used herein are intended to include every number and subset of numbers contained within that range, whether specifically disclosed or not. Further, these numerical ranges should be construed as providing support for a claim directed to any number or subset of numbers in that range.

As used herein, the words "preferred," "preferably" and variants thereof refer to embodiments of the invention that afford certain benefits, under certain circumstances. However, other embodiments can also be preferred, under the same or other circumstances. Furthermore, the recitation of one or more preferred embodiments does not imply that other embodiments are not useful, and is not intended to exclude other embodiments from the scope of the invention.

References herein to "one embodiment," or "one aspect" or "one version" or "one objective" or "another embodiment," or "another aspect" or "another version" or "another objective" or "one of the objective" of the invention can include one or more of such embodiment, aspect, version or objective, unless the context clearly dictates otherwise. Furthermore, the recitation of "one embodiment" or "another embodiment" does not imply that other embodiments are not useful, and is not intended to exclude other embodiments from the scope of the invention.

The term "pH" refers to a measure of the acidity or basicity of an aqueous solution. Pure water is considered to be neutral, with a pH close to 7.0 at 25° C. Solutions with a pH less than 7 are considered to be acidic and solutions with a pH greater than 7 are considered to be basic or alkaline.

The term "substantially anhydrous" or "very low water" are interchangeably used and there refers to a state of not being aqueous in nature. The term "substantially anhydrous" generally mean or inform that the water is deliberately added to the composition in any a low quantity. However, the term "substantially anhydrous" does not mean that low amounts of water cannot be present, for example as a consequence of its association with hygroscopic raw materials. Accordingly, for the purposes of this invention, the term "substantially anhydrous" generally refers that water is present in an amount between about 0.1% to about 10%, more particularly about 0.2% to 7% by weight based on the total weight of the thickener composition.

The term "chelating agent" also called chelators or sequestrants refers to a compound that is capable of forming a complex wherein a metal ion is bonded to two or more atoms of the chelating agent.

The term "polyphosphate" refers to a group having two or more phosphate groups arranged primarily in a linear configuration, although some cyclic derivatives can be present.

The term "dentifrice" refers to pastes, gels, or liquid formulations unless otherwise specified. The dentifrice composition can be a single-phase composition or can be a combination of two or more dentifrice compositions. The dentifrice composition can be in any desired form, such as deep striped, surface striped, multilayered, having the gel surrounding the paste, or any combination thereof. Each dentifrice composition in a dentifrice comprising two or more separate dentifrice compositions can be contained in a physically separated compartment of a dispenser and dispensed side-by-side.

The term "oral care composition" refers to a product which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral composition of the present application can be in the form of a toothpaste, dentifrice, tooth powder, topical oral gel, mouth rinse, denture product, mouth spray, lozenge, oral tablet, or chewing gum.

The term "orally acceptable additive" refers to any safe and effective materials for use in the oral care compositions of the present application. Such materials include but are not limited to pH adjusting agents and/or buffers, humectants, polishing agents, fluoride ion sources, flavoring agents, sweetening agents, surfactants, antibacterial agents, anti-inflammatory agents, whitening agents, anti-caries agents, enamel repair agents, anti-sensitivity agents, breath freshening agents, foaming agents, solubilizing agents, tartar control or anti-calculus agents, or anti-stain ingredients, anti-erosion agents, opacifying agents, enzymes, sensate ingredients, stabilizers, coloring agents, abrasive compounds, rheology modifiers and binders, foaming agents and combinations thereof. Such additives are well known in the art.

The terms "tartar" and "calculus" are used interchangeably and refer to mineralized dental plaque deposits.

The term "teeth" refers to natural teeth as well as artificial teeth or dental prosthesis.

The term "dispenser" refers to any pump, tube, or container suitable for dispensing toothpaste.

The present application provides a substantially anhydrous thickener system in the form of a gel for use in oral care compositions that comprises ingredients which are sensitive to water. The present application relates to a substantially anhydrous thickener system for use in oral care compositions comprising: (i) carboxymethyl cellulose or its salts thereof, (ii) a chelating agent, (iii) optionally hydroxyethyl cellulose in a solvent system, wherein the thickener system is heated to a temperature ranging from about 70° C. to about 120° C. to form the gel.

According to one of the embodiment of the present application, carboxymethyl cellulose and its salts has a different degree of polymerization with an average degree of polymerization from 300 to 4,800, corresponding to a molecular weight range of 70,000 g/mol to 1,100,000 g/mol.

According to another embodiment of the present application, carboxymethyl cellulose and its salts has a different degree of polymerization with an average degree of polymerization from about 800 to about 1,800; from about 1800 to about 2,800; or from about 2800 to about 3,800.

According to another embodiment, carboxymethyl cellulose and its salts has a molecular weight ranging from about 100,000 g/mol to about 1,000.000 g/mol. Other ranges of molecular weights include but not limited to from about 100,000 g/mol to about 200,000 g/mol; 200,000 g/mol to about 300,000 g/mol; 300,000 g/mol to about 400,000 g/mol; 400,000 g/mol to about 500.000 g/mol; 500,000 g/mol to about 600,000 g/mol; 600,000 g/mol to about 700.000 g/mol; 700,000 g/mol to about 800,000 g/mol; 800,000 g/mol to about 900,000 g/mol; 900,000 g/mol to about 1000,000 g/mol.

According to one embodiment of the present application, carboxymethyl cellulose and its salts has a different degree of polymerization with an average degree of polymerization from about 1200 to about 2,400. Other possible degree of polymerization would include but not limited to from about 1200 to about 1400; from about 1400 to about 1,600; from about 1600 to about 1,800; from about 1800 to about 2,000; from about 2000 to about 2,200); or from about 2,200 to about 2,400;

According to another embodiment, carboxymethyl cellulose and its salts has a molecular weight ranging from about 300,000 g/mol to about 700,000 g/mol. Other ranges of molecular weights include but not limited to from about 300,000 g/mol to about 400,000 g/mol; from about 400,000 g/mol to about 500,000 g/mol; from about 500,000 g/mol to about 600.000 g/mol; or from about 600,000 g/mol to about 700,000 g/mol.

According to another embodiment of the present application, the carboxymethyl cellulose and its salts are readily available from commercial sources, however, the following non-limiting commercial products/tradenames include Aqualon CMC-7M grades, Aqualon CMC-7H grades and Aqualon CMC-9M grades from Ashland LLC.

According to yet another embodiment, the carboxymethyl cellulose (CMC) and its salts is present in an amount from about 0.05% to about 10% by weight of the thickener system. In another embodiment, other the possible ranges of CMC would include but not limited to from about 0.05 wt. % to about 1.0 wt. %; from about 1.0 wt. % to about 2.0 wt. %; from about 2.0 wt. % to about 3.0 wt. %; from about 3.0 wt. % to about 4.0 wt. %; from about 4.0 wt. % to about 5.0 wt. %; from about 5.0 wt. % to about 6.0 wt. %; from about 6.0 wt. % to about 7.0 wt. %; from about 7.0 wt. % to about 8.0 wt. %; from about 8.0 wt. % to about 9.0 wt. %; or from about 9.0 wt. % to about 10.0 wt. %.

According to one embodiment of the present application, the carboxymethyl cellulose and its salts is present in an amount from about 1% to about 8% by weight of the thickener system. Other non-limiting ranges would include but not limited to 2%, 3%, 4%, 5%, 6%, 7% or 8% by weight of the thickener system.

According to one of the embodiment, the chelating agent is selected from the group consisting of disodium pyrophosphate, dipotassium pyrophosphate, tetrapotassium pyrophosphates, tetrasodium pyrophosphates, disodium ethane-1-hydroxy-1,1-diphosphonate (EHDP), methanediphosphonic acid, 2-phosphonobutane-1,2,4-tricarboxylic acid, citric acid, sodium citrate, potassium citrate, tartaric acid, disodium calcium ethylene diamine tetraacetic acid, disodium ethylene diamine tetraacetate, disodium ethylene diamine tetraacetic acid, gluconic acid, methyl vinyl ether and maleic anhydride (PVM/MA) copolymers, polyacrylic acid, polyitaconic acid and combinations thereof.

According to one of the embodiment, the chelating agent is present in an amount from about 0.01% to about 10% by weight of the thickener system.

According to another embodiment, the chelating agent is present in an amount from about 0.1% to about 8% by weight of the thickener system.

According to one of the embodiment, the chelating agent is present in an amount from about 0.5% to about 5% by weight of the thickener system.

According to one of the embodiment, hydroxyethyl cellulose has a different degree of polymerization with an average degree of polymerization from about 300 to about 4,800, corresponding to a molecular weight ranging from about 90,000 g/mol to about 1,300,000 g/mol.

According to another embodiment, hydroxyethyl cellulose has a different degree of polymerization with an average degree of polymerization from about 800 to about 3,800

According to another embodiment, hydroxyethyl cellulose has a molecular weight ranging from about 100,000 g/mol to about 1,000,000 g/mol.

According to one embodiment, hydroxyethyl cellulose has a different degree of polymerization with an average degree of polymerization from 1200 to 2,400.

According to another embodiment, hydroxyethyl cellulose has a molecular weight range of 300,000 g/mol to 700,000 g/mol.

According to another embodiment of the present application, the hydroxyethyl cellulose is readily available from commercial sources, the non-limiting commercial products are Natrosol 250 M, Natrosol 250 HX, and Natrosol Plus CS 330 from Ashland LLC.

According to one embodiment, the hydroxyethyl cellulose is present in an amount of from about 0.05% to about 10% by weight of the thickener system. In another embodiment, other the possible ranges of CMC would include but not limited to from about 0.05 wt. % to about 1.0 wt. %; from about 1.0 wt. % to about 2.0 wt. %; from about 2.0 wt. % to about 3.0 wt. %; from about 3.0 wt. % to about 4.0 wt. %; from about 4.0 wt. % to about 5.0 wt. %; from about 5.0 wt. % to about 6.0 wt. %; from about 6.0 wt. % to about 7.0 wt. %; from about 7.0 wt. % to about 8.0 wt. %; from about 8.0 wt. % to about 9.0 wt. %; or from about 9.0 wt. % to about 10.0 wt %.

According to another embodiment, the hydroxyethyl cellulose is present in an amount from about 1% to about 8% by weight of the thickener system. Other non-limiting ranges would include but not limited to 2%, 3%, 4%, 5%, 6%, 7% or 8% by weight of the thickener system.

A solvent or solvent system can be selected from the group consisting of water, glycerin, diglycerin, sorbitol, lactitol, xylitol, propylene glycol, polyethylene glycol and combinations thereof.

According to another embodiment, the solvent system is present in an amount from about 60% to about 99.9% by weight of the thickener system. In another embodiment, other the possible ranges of solvent system would include but not limited to from about 60 wt. % to about 70 wt. %; from about 70 wt. % to about 80 wt. %; from about 80 wt. % to about 90 wt. %; from about 90 wt. % to about 99.9 wt. %.

According to another embodiment, water present in an amount from about 0.1% to about 10% by weight of the thickener system. In another embodiment, other the possible ranges of water would include but not limited to from about 0.1 wt. % to about 1.0 wt. %; from about 1.0 wt. % to about 2.0 wt. %; from about 2.0 wt. % to about 3.0 wt. %; from about 3.0 wt. % to about 4.0 wt. %; from about 4.0 wt. % to about 5.0 wt. %; from about 5.0 wt. % to about 6.0 wt. %; from about 6.0 wt. % to about 7.0 wt. %; from about 7.0 wt. to about 8.0 wt. %; from about 8.0 wt. % to about 9.0 wt. %; or from about 9.0 wt. % to about 10.0 wt. %.

According to another embodiment, water present in an amount from about 0.5% to about 7% by weight of the thickener system.

One more embodiment of the present application relates to a substantially anhydrous thickener system in the form of a gel for use in oral care compositions comprising: (i) carboxymethyl cellulose or its salts thereof, (ii) a chelating agent, and (iii) optionally hydroxyethyl cellulose, in a solvent system, wherein the thickener system is heated to a temperature ranging from about 70° C. to about 120° C. to form a gel.

According to another embodiment, the present application relates to a substantially anhydrous thickener system for use in oral care compositions comprising: (i) carboxymethyl cellulose or its salts thereof, (ii) disodium pyrophosphate, in a solvent system of a mixture of water, glycerin, propylene glycol and polyethylene glycol, wherein the thickener system is heated to a temperature ranging from about 70° C. to about 120° C. to form the gel.

According to another embodiment, the present application discloses a substantially anhydrous thickener system for use in oral care compositions comprising: (i) carboxymethyl cellulose or its salts thereof, (ii) disodium pyrophosphate and (iii) hydroxyethyl cellulose, in a solvent system of a mixture of water, glycerin, propylene glycol, and polyethylene glycol, wherein the thickener system is heated to a temperature ranging from about 70° C. to about 120° C. to form the gel.

According to another embodiment, the present application relates to a substantially anhydrous thickener system in the form of a gel for use in oral care compositions comprising: (i) a mixture from about 0.1% to about 10% w/w of carboxymethyl cellulose or its salts thereof and hydroxyethyl cellulose. (ii) disodium pyrophosphate in an amount from about 0.01% to about 2% w/w, and (iii) a solvent system in an amount from about 50% to about 90% w/w of a mixture of water, glycerin, propylene glycol, and polyethylene glycol, wherein the thickener system is heated to a temperature ranging from about 70° C. to about 120° C. to form the gel.

One embodiment of the present application relates to a method of preparing the thickener system for use in oral care compositions comprising the steps of: (a) charging carboxymethyl cellulose or its salts thereof into a reaction container, (b) dissolving the mixture of "(a)" in a solvent system; (c) charging a chelating agent into (b); and (d) heating the resultant of (c) to a temperature of 80° C. for at least about 10 minutes.

According to one of the embodiment, the present application relates to a method of preparing the thickener system for use in oral care compositions comprising the steps of: (a) charging a mixture of carboxymethyl cellulose or its salts thereof and hydroxyethyl cellulose into a reaction container, (b) dissolving the mixture of "(a)" in a solvent system, (c) charging a chelating agent into (b), and (d) heating the resultant of (c) to a temperature of 80° C. for at least about 10 minutes.

According to another embodiment, the present application relates to an oral care composition comprising: (i) a substantially anhydrous thickener system in the form of a gel comprising: carboxymethyl cellulose or its salts thereof. (ii) a chelating agent, and (ii) optionally hydroxyethyl cellulose, in a solvent system, wherein the thickener system is heated to a temperature ranging from about 70° C. to about 120° C. to form a gel; and ii) one or more orally acceptable additives.

According to another embodiment, the present application is an oral care composition comprising: (A) from about 50 to about 90% w/w of a substantially anhydrous thickener system comprising: (i) carboxymethyl cellulose or its salts thereof, (ii) a chelating agent, and (iii) hydroxyethyl cellulose, in a solvent system, wherein the thickener system is heated to a temperature ranging from about 70° C. to about 120° C. to form a gel; and (B) from about 10 to about 50% w/w of one or more orally acceptable additives.

The orally acceptable additive according to present application can be selected from the group consisting of pH adjusting agents and/or buffers, humectants, polishing agents, fluoride ion sources, flavoring agents, sweetening agents, surfactants, rheology modifying agents, antibacterial agents, anti-inflammatory agents, whitening agents, anti-caries agents, enamel repair agents, breath freshening agents, foaming agents, solubilizing agents, tartar control agents, anti-stain ingredients, anti-erosion ingredients, opacifying agents, enzymes, sensate ingredients, stabilizers, coloring agents, abrasive compounds, foaming agents and combinations thereof.

The pH of the present compositions can be adjusted through the use of a "pH adjusting agent" or "buffering agent". Buffering agents or pH adjusting agents, as used herein, refer to agents that can be used to adjust the pH of the composition to a range of about pH 4.0 to about pH 9.0. Buffering agents or pH adjusting agent include monosodium phosphate, trisodium phosphate, sodium hydroxide, sodium carbonate, sodium acid pyrophosphate, citric acid, and sodium citrate. Buffering agents can be administered at a level of from about 0.5% to about 10%, by weight of the present oral care compositions.

The oral care compositions typically further comprise humectants. Humectants serve to keep toothpaste compositions from hardening upon exposure to air, to give compositions a moist feel to the mouth, and, for particular humectants, to impart desirable sweetness of flavor to toothpaste compositions. The humectant, on a pure humectant basis, generally comprises from about 0% to about 70% of the oral care compositions. According to another embodiment, the humectant can be present from about 20% to about 50%, by weight of the compositions herein. Suitable humectants for use in the oral care compositions include edible polyhydric alcohols such as glycerin, sorbitol, xylitol, butylene glycol, polyethylene glycol, and propylene glycol, especially sorbitol, and glycerin.

The polishing agent for the purpose of the present application is selected from the group consisting of silicas, insoluble sodium polymetaphosphate, hydrated alumina, calcium carbonate, dicalcium orthophosphate dihydrate, calcium pyrophosphate, tricalcium phosphate, calcium polymetaphosphate, resinous abrasive materials, and mixtures thereof.

Non-limiting polishing agents such as colloidal silica, sold under the trademark SYLOID as Syloid 72 and Syloid 74 or under the trademark SANTOCEL as SANTOCEL 100 or alkali metal aluminosilicate complexes (that is, silica containing alumina combined in its matrix) are useful, since they are consistent with gel-like texture and have refractive indices close to the refractive indices of gelling agent-liquid (including water and/or humectant) systems commonly used in dentifrices.

The oral care compositions may comprise about 1 to about 20% of a polishing agent or abrasive, including but not limited to a silica abrasive, by weight. According to another embodiment, other possible ranges of polishing agent or abrasive would include but not limited to from about 1 wt. % to about 5 wt. %; from about 5 wt. % to about 10 wt. %; from about 10 wt. % to about 15 wt. %; from about 15 wt. % to about 20 wt. %.

The compositions of the disclosure can include abrasives and/or whitening agents, which can include any suitable silica abrasive, such as sodium metaphosphate, potassium metaphosphate, tricalcium phosphate, calcium phosphate dehydrate, anhydrous dicalcium phosphate, calcium pyrophosphate, magnesium orthophosphate, trimagnesium phosphate, calcium carbonate, baking soda, sodium hexametaphosphate, magnesium carbonate, magnesium silicate, titanium dioxide, zinc oxide, aluminum silicate, zirconium silicate, hydrated/calcined alumina, bentonite, hydrated silica, amorphous silica, silica gel or colloidal silica, alkali metal aluminosilicate complexes, silicon dioxide, alumina, hydroxyapatite, dicalcium phosphate dihydrate and any combination thereof.

The oral care compositions also typically contains a source of fluoride ions, or fluorine-providing component, as anti-caries agent, in an amount sufficient to supply about 25 ppm to 5,000 ppm of fluoride ions. These compounds can be slightly soluble in water or can be fully water-soluble. They are characterized by their ability to release fluoride ions in water and by substantial freedom from undesired reaction with other compounds of the oral preparation. Among these materials are inorganic fluoride salts, such as soluble alkali metal, alkaline earth metal salt. For example, sodium fluoride, potassium fluoride, ammonium fluoride, calcium fluoride, a copper fluoride such as cuprous fluoride, zinc fluoride, barium fluoride, sodium fluorosilicate, ammonium fluorosilicate, sodium fluorozirconate, ammonium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate (MFP) and mixtures thereof. Also, organic fluoride compounds such as amine fluoride (Olaflur).

The amount of fluoride-providing compound is dependent to some extent upon the type of compound, its solubility, and the type of oral preparation, but it must be a non-toxic amount, generally about 0.0005 to about 3.0% in the preparation of dentifrice, e.g. dental gel and an amount of such compound which releases up to about 5,000 ppm of fluoride ion by weight of the preparation is considered satisfactory. Any suitable minimum amount of such compound can be used, but it is typical to employ sufficient compound to release about 300 to 2,000 ppm. According to one embodiment, the release is in the range from about 800 to about 1,500 ppm of fluoride ion. The other ranges are from about 900 to about 1000 ppm; from about 1000 to about 1,100 ppm; from about 1100 to about 1,200 ppm; from about 1200 to about 1,300 ppm; from about 1300 to about 1,400 ppm; and from about 1400 to about 1,500 ppm.

Typically, in the cases of alkali metal fluorides, the component is present in an amount up to about 5% by weight, based on the weight of the preparation. According to another embodiment, the amount is from about 0.05% to about 1%. In the case of sodium monofluorophosphate, the compound can be present in an amount of about 0.1-3%, more typically about 0.3-0.6%.

The oral care compositions can further comprise flavoring and sweetening agents. Suitable flavoring agents include wintergreen oil, peppermint oil, spearmint oil, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof. Flavoring agents are generally used in the compositions at levels of from about 0.001% to about 5%, by weight of the composition.

The sweetening agents which can be used include sucrose, glucose, saccharin, dextrose, levulose, lactose, mannitol, sorbitol, fructose, maltose, xylitol, saccharin salts, thaumatin, aspartame, D-tryptophan, dihydrochalcones, potassium acesulfame, sucralose and cyclamate salts, especially sodium cyclamate and sodium saccharin, and mixtures thereof. A composition contains from about 0.1% to about 10% of these agents. According to another embodiment, the composition contains from about 0.1% to about 1%, by weight of the composition.

In addition to flavoring and sweetening agents, coolants, salivating agents, warming agents, and numbing agents can be used as optional ingredients in compositions of the present application based on their necessity and type of formulation. These agents are present in the compositions at a level of from about 0.001% to about 10%. According to another embodiment, these agents are present in an amount from about 0.1% to about 1%, by weight of the composition.

The oral care compositions can further comprise surfactants which are reasonably stable and foam throughout a wide pH range. The surfactant can be anionic, nonionic, amphoteric, zwitterionic, cationic, or mixtures thereof.

The anionic surfactants include water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms, such as sodium lauryl sulfate and sodium coconut monoglyceride sulfonate. Other suitable anionic surfactants are sarcosinates, such as sodium lauryl sarcosinate, taurates, sodium lauryl sulfoacetate, sodium lauryl isethionate, sodium lauryl sulfonate, sodium lauryl carboxylate, and sodium dodecyl benzenesulfonate, and mixtures thereof. The oral care compositions further comprise an anionic surfactant in an amount from about 0.025% to about 9%. According to another embodiment, the anionic surfactant is present in an amount from about 0.05% to about 5%, and most preferably from about 0.2% to about 3%.

Another contemplated surfactant is selected from the group consisting of sarcosinate surfactants, isethionate surfactants and taurate surfactants. The surfactants include, but are not limited to alkali metal or ammonium salts of these surfactants. The surfactants can be sodium and potassium salts of lauroyl sarcosinate, myristoyl sarcosinate, palmitoyl sarcosinate, stearyl sarcosinate, and oleoyl sarcosinate. These surfactants can be present in the oral care compositions in an amount from about 0.1% to about 2.5%, from about 0.3% to about 2.5%, and from about 0.5% to about 2.0% by weight of the total composition.

Cationic surfactants include, but are not limited to, derivatives of aliphatic quaternary ammonium compounds having one long alkyl chain containing from about 8 to 18 carbon atoms such as lauryl trimethylammonium chloride; cetyl pyridinium chloride; cetyl trimethylammonium bromide; di-isobutylphenoxyethyl-dimethylbenzylammonium chloride; coconut alkyltrimethylammonium nitrite; cetyl pyridinium fluoride; etc. Certain cationic surfactants can also act as germicides.

Nonionic surfactants useful in the oral care compositions are compounds produced by the condensation of alkylene oxide groups (hydrophilic in nature) with an organic hydrophobic compound which can be aliphatic or alkylaromatic in nature. Examples of suitable nonionic surfactants include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials. According to another embodiment, the surfactant including but not limited to zwitterionic derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate.

The oral care compositions may further comprise surfactants including, but not limited to, alkyl dimethyl betaines. The alkyl dimethyl betaines include decyl betaine or 2-(N-decyl-N,N-dimethylammonio) acetate, coco betaine or 2-(N-coc-N, N-dimethyl ammonio) acetate, myristyl betaine, palmityl betaine, lauryl betaine, cetyl betaine, cetyl betaine, stearyl betaine, etc. The amido-betaines are exemplified by cocoamidoethyl betaine, cocoamidopropyl betaine, lauramidopropyl betaine and the like.

Examples of antibacterial agents include, but are not limited to, zinc salts, stannous salts, cetyl pyridinium chloride, chlorhexidine, triclosan, triclosan monophosphate, and flavor oils. Zinc salt such as zinc Lactate. Soluble stannous salts, such as stannous fluoride, stannous chloride, stannous acetate, sodium stannous fluoride, potassium stannous fluoride, stannous hexafluorozirconate, stannous sulphate, stannous tartrate, stannous gluconate and others, have been used in the compositions. Triclosan is one of the anti-bacterial agent of the application, utilized in amounts of about 0.03% to about 0.6% by weight of the total oral care composition.

Anti-caries agents such as stannous fluoride, sodium and potassium fluoride, sodium and potassium monofluorophosphate. One of the example is sodium fluoride, can be incorporated into the oral care compositions in amounts well known in the art. The fluoride compositions prevent formation of cavities and strengthen the enamel surface.

Preservatives which can be used in the oral care formulations of the invention include those conventionally employed in the an, such as benzoic acid and sodium benzoate; the parabens; sorbic acid and sorbates; propionic acid and propionates; acetic acid and acetates; nitrates and nitrites; sulfur dioxide and sulfites; antibiotics; diethyl pyrocarbonate; epoxides; hydrogen peroxide; and phosphates. The parabens include the methyl, ethyl, propyl, and butyl esters of parahydroxybenzoic acid.

The coloring agents are used to create the preferred color. The coloring agents or colorants used in the present application include natural foods colors and dyes suitable for food, drug and cosmetic applications. These colorants are also known as F.D. & C. dyes and lakes and are water-soluble in nature. Examples of representative colorants include, but are not limited to, disodium salt of 5,5-indigotindisulfonic acid (Blue No. 2), 4-[4-(N-ethyl-p-sulfonium-benzylamino) diphenylmethylene]-[1-(N-ethyl-N-p-sulfoniumbenzyl)delta-2,5-cyclohexadien eimine] (Green No. 1), Yellow No. 10, Green No. 3 comprising a triphenylinethane dye, FD&C Blue #1, FD&C Yellow #5, FD&C Yellow #10, FD&C Red #3, FD&C Red #40; caramel color or powder (#05439), chocolate shade (#05349), green lake blend (#09236), kowet titanium dioxide (#03970), yellow liquid color (#00403), and nitrites. A full recitation of all F.D. & C. and D. & C. dyes and their corresponding chemical structures can be found in the irk-Othmer Bncyclopedia of Chemical Technology, Volume 5, pages 857-884, which text is accordingly incorporated herein by reference. The colorant of the present application is caramel color. These coloring agents can be incorporated in amount up to about 3%, more particularly up to about 2%, and in some cases less than about 1% by weight of the oral care mouthwash compositions.

The rheology modifiers of the present application include, but are not limited to, polysaccharides (e.g., carrageenan, hyaluronic acid, glucosaminoglycan), biopolymers (e.g., xanthan gum), synthetic polymers, and abrasive/thickening silicas.

The stabilizing agents of the present application include, but are not limited to, sodium gluconate.

According to one embodiment, pH of the oral care composition ranges from about 4 to about 9.

In accordance with one embodiment of the present application, the oral care composition of the present application can be formulated in any of several required forms according to their necessity, and the non-limiting forms include a paste, powder, gel or liquid.

Further, certain aspects of the present invention are illustrated in detail by way of the following examples. The examples are given herein for illustration of certain aspects of the invention and are not intended to be limiting thereof.

EXAMPLES

The thickener systems and toothpaste compositions in the following examples were prepared by a hot process, in which a gel phase is first formed. The thickener systems can then be processed further into full toothpaste formulations using a Ross™ Mixer, which is a well-known double planetary gear, two paddle mixer which operates at 5 to 100 revolutions per minute and can be operated under vacuum. More detailed descriptions of the method of manufacture for various compositions are shown below.

Numerous runs or experimental batches were conducted using the hot process described herein. The Tables (1-3) below, show of examples of compositions which use thickening systems of sodium carboxymethyl cellulose with hydroxyethyl cellulose and, iota carrageenan with xanthan gum, with and without different acidic chelating agents. Compositions were evaluated for viscosity, using a Brookfield viscometer and for toothpaste bead stand-up, using the Cuban Rack test.

Example 1: Procedure for Making Anhydrous Thickener Systems (1) In a suitable vessel, glycerin, PEG-400 and propylene glycol at room temperature were mixed using a Greerco 1-L homogenizer at 25% speed for 5-10 minutes. (2) thickening gums (Aqualon CMC 7MXF and Natrosol HEC 250 MX) were mixed to the solvent system and then mixed with the Greerco 1-L homogenizer at 25% speed for 5-10 minutes. (3) water was to the above mixture, mixed at 25% speed for 5-10 minutes at room temperature and then bring the temperature of the mixture up to 70°-85° C. for about 15-30 while mixing. (4) When the mixture has reached 70°-85° C., added the chelating agent i.e., disodium pyrophosphate and mixed at 25% speed until the thickening gums is fully dispersed and gelled for about at least 10 minutes. The total ingredients composition is as per the Table 1.

EXAMPLES 2-7 were prepared according to the procedure of EXAMPLE 1 with compositions specified in Table 1.

TABLE 1

Anhydrous Thickener Systems:

| Ingredient | Ex. 1 | Ex. 2 | Ex. 3 | Ex. 4 | Ex. 5 | Ex. 6 | Ex. 7 |
|---|---|---|---|---|---|---|---|
| | Compositions w/w (%) | | | | | | |
| Glycerin | 75.59 | 74.92 | 74.92 | 74.62 | 75.49 | 75.79 | 76.46 |
| PEG-400 | 7.58 | 7.58 | 7.58 | 7.58 | 7.58 | 7.58 | 7.58 |
| Propylene Glycol | 7.58 | 7.58 | 7.58 | 7.58 | 7.58 | 7.58 | 7.58 |
| Water | 7.58 | 7.58 | 7.58 | 7.58 | 7.58 | 7.58 | 7.58 |
| Aqualon CMC 7MXF | 1.00 | 1.00 | 1.00 | 1.00 | 1.00 | — | — |
| Natrosol HEC 250 MX | 0.67 | 0.67 | — | 0.67 | 0.67 | — | — |
| Natrosol HEC 250 HX | — | — | 0.67 | — | — | — | — |
| Xanthan Gum | — | — | — | — | — | 0.4 | 0.4 |
| Carrageenan (iota) | — | — | — | — | — | 0.4 | 0.4 |
| Disodium Pyrophosphate | — | 0.67 | 0.67 | — | — | 0.67 | — |
| Citric acid | — | — | — | 0.30 | — | — | — |
| Phosphoric acid | — | — | — | — | 0.10 | — | — |
| Total: | 100.0 | 100.0 | 100.0 | 100.0 | 100.00 | 100.00 | 100.00 |
| pH (diluted 1:1) with water) | 7.0 | 5.0 | 5.0 | 4.5 | 4.2 | 5.0 | 6.8 |

Figure 1:
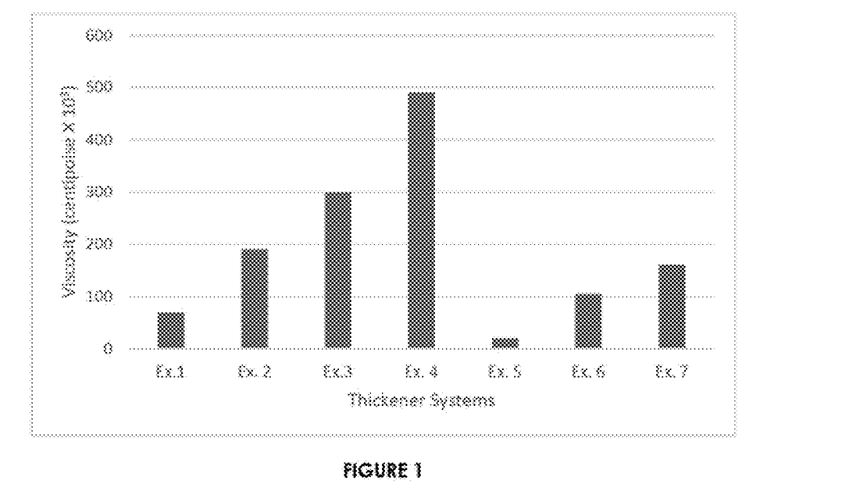
FIG. 1: Viscosity of Anhydrous Thickener Systems EXAMPLES 1-7.
Figure 2:
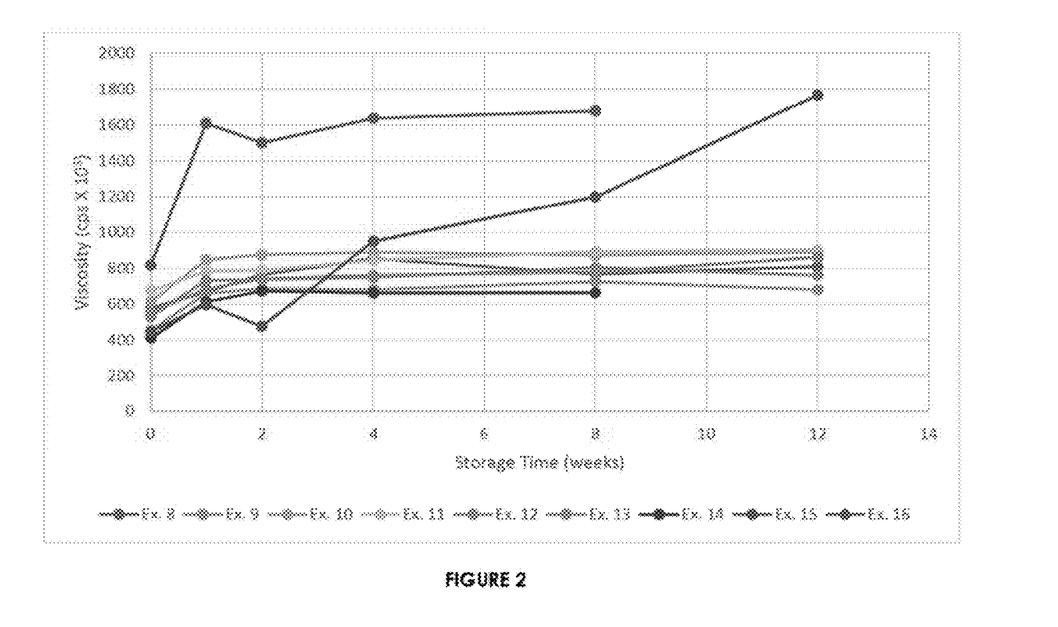
FIG. 2: Toothpaste Compositions (EXAMPLES 8-16) Viscosity vs. Storage Time (45° C. storage condition).

Test Methods: Viscosity measurements were taken at 25° C. using a Brookfield™ Model DV2T viscometer, fitted with a suitable T-bar spindle in the Helipath mode at 2 RPM. The choice of T-bar spindle selected (TB, TC, TD or TE) was made based on the optimal viscosity range of the spindle. The viscosity of thickener systems was plotted against each formulation in FIG. 1.

Example 8: Tooth Paste Compositions Containing Anhydrous Thickener Systems

TABLE 2

Example 8: Tooth Paste Compositions Containing Anhydrous Thickener Systems:

| Ingredient | Ex. 8 | Ex. 9 | Ex. 10 | Ex. 11 | Ex. 12 | Ex. 13 | Ex. 14 | Comparative Ex. 15 | Ex. 16 |
|---|---|---|---|---|---|---|---|---|---|
| | Compositions W/W (%) | | | | | | | | |
| Glycerin 99.5% | 58.21 | 58.46 | 58.36 | 58.36 | 58.36 | 58.21 | 58.01 | 58.36 | 58.21 |
| Deionized water | 5.36 | 5.36 | 5.36 | 5.36 | 5.36 | 5.36 | 5.36 | 5.36 | 5.36 |
| PEG-400 | 5.12 | 5.12 | 5.12 | 5.12 | 5.12 | 5.12 | 5.12 | 5.12 | 5.12 |
| Propylene Glycol | 5.12 | 5.12 | 5.12 | 5.12 | 5.12 | 5.12 | 5.12 | 5.12 | 5.12 |
| Aqualon CMC 7MXF | 0.30 | — | — | — | — | 0.30 | 0.30 | — | 0.45 |
| Aqualon CMC 7HXF | — | 0.20 | 0.30 | 0.30 | 0.30 | — | — | — | 0.30 |
| Natrosol HEC 250M | 0.45 | 0.30 | — | 0.30 | — | 0.45 | 0.45 | — | — |
| Natrosol HEC 250 HX | — | — | 0.30 | — | — | — | — | — | — |
| Natrosol Plus (cetyl hydroxyethylcellulose) | — | — | — | — | 0.30 | — | — | — | — |
| Xanthan Gum | — | — | — | — | — | — | — | 0.30 | — |
| Carrageenan (Iota) | — | — | — | — | — | — | — | 0.30 | — |

TABLE 2-continued

Example 8: Tooth Paste Compositions Containing Anhydrous Thickener Systems:

| Ingredient | Ex. 8 | Ex. 9 | Ex. 10 | Ex. 11 | Ex. 12 | Ex. 13 | Ex. 14 | Comparative Ex. 15 | Ex. 16 |
|---|---|---|---|---|---|---|---|---|---|
| | Compositions W/W (%) | | | | | | | | |
| Disodium Pyrophosphate | 0.10 | 0.10 | 0.10 | 0.10 | 0.10 | — | — | 0.10 | 0.10 |
| Citric Acid | — | — | — | — | — | 0.10 | — | — | |
| PVM/MA | — | — | — | — | — | — | 0.30 | — | |
| Abrasive silica | 20.00 | 20.00 | 20.00 | 20.00 | 20.00 | 20.00 | 20.00 | 20.00 | 20.00 |
| Thickening silica | 2.00 | 2.00 | 2.00 | 2.00 | 2.00 | 2.00 | 2.00 | 2.00 | 2.00 |
| Peppermint Flavor Oil | 1.00 | 1.00 | 1.00 | 1.00 | 1.00 | 1.00 | 1.00 | 1.00 | 1.00 |
| Sodium Fluoride | 0.24 | 0.24 | 0.24 | 0.24 | 0.24 | 0.24 | 0.24 | 0.24 | 0.24 |
| Titanium Dioxide | 0.30 | 0.30 | 0.30 | 0.30 | 0.30 | 0.30 | 0.30 | 0.30 | 0.3 |
| Sodium Saccharin | 0.30 | 0.30 | 0.30 | 0.30 | 0.30 | 0.30 | 0.30 | 0.30 | 0.3 |
| Sodium Lauryl Sulfate | 1.50 | 1.50 | 1.50 | 1.50 | 1.50 | 1.50 | 1.50 | 1.50 | 1.50 |
| Total: | 100.00 | 100.00 | 100.00 | 100.00 | 100.00 | 100.00 | 100.00 | 100.00 | 100.00 |
| Initial Viscosity (centipoise) | 576,000 | 452,000 | 612,000 | 674,000 | 554,000 | 529,000 | 410,000 | 445,000 | 817,000 |

The thickener system of EXAMPLE 1 is transferred to a 1 quart Ross™ double planetary mixer, titanium dioxide and the silicas were added the and mixed under a minimum of 28" Hg vacuum at 80 RPM for 20-25 minutes. (3) sodium lauryl sulfate is added to the mixing bowl and mix under a minimum of 28" Hg vacuum at 10 RPM for 5-10 minutes. (4) Finally, flavor oil is added to the Ross™ mixing bowl and mixed under a minimum of 28" vacuum at 50 RPM for 5-6 minutes. The finished product should be packaged in the appropriate container.

EXAMPLES 9-16 were prepared in a similar procedure of EXAMPLE 8 with compositions of Table 2. Example 15 is a comparative example and demonstrates the thickener system described herein demonstrated unexpectedly better performance than a prior art thickener containing xanthan gum and carrageenan.

Examples 17-18: Additional Tooth Paste Compositions Containing Anhydrous Thickener Systems A tooth whitening and anti-cavity, gum health tooth paste compositions were prepared according to the procedure of EXAMPLE 8 as per the compositions specified in Table 3.

TABLE 3

Additional Tooth Paste Compositions:

| Ingredient | Ex. 17: Tooth Whitening | Ex. 18: Anti-Cavity, Gum Health |
|---|---|---|
| | Composition % w/w | |
| Glycerin 99.5% | Q.S. | Q.S. |
| Deionized water | 5.36 | 5.36 |
| PEG-400 | 5.12 | 5.12 |
| Propylene Glycol | 5.12 | 5.12 |
| Disodium Pyrophosphate | 0.10 | 0.10 |
| Aqualon CMC | 0.30 | 0.30 |
| Natrosol HEC | 0.30 | 0.45 |
| Abrasive silica | 20.00 | 20.00 |
| Thickening silica | 2.00 | 2.00 |
| Peppermint Flavor Oil | 1.00 | 1.00 |
| Zinc Lactate | 0 | 2.00 |
| Sodium Hexametaphosphate | 15.00 | 7.00 |
| Sodium Gluconate | 0 | 1.00 |
| Sodium Fluoride | 0.24 | 0 |
| Stannous Chloride | 0 | 0.40 |
| Stannous Fluoride | 0 | 0.45 |
| Titanium Dioxide | 0.30 | 0.30 |
| Sodium Saccharin | 0.30 | 0.30 |
| Sodium Lauryl Sulfate | 1.50 | 1.50 |
| Total: | 100.00 | 100.00 |

Figure 3:
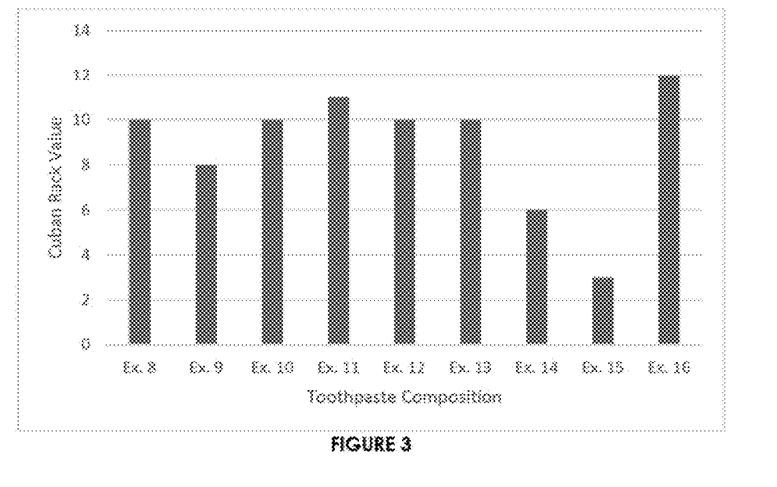
FIG. 3: Toothpaste Compositions (EXAMPLES 8-16) Cuban Rack Test Values.

Cuban Rack Test Method:

Full toothpaste formulations were packaged into tubes and the toothpaste ribbon integrity ('stand-up') was measured using the Cuban Rack test. In this test, the paste is squeezed from a tube through a fixed orifice across a grid of parallel rods, increasingly spaced apart. The test results are expressed as the greatest space number (numbers are from 1-12) which represents the longest distance between rods that support the dentifrice ribbon without having it break. Higher Cuban Rack test values indicate better toothpaste ribbon stand-up. The Cuban Rack test was run as follows: The nozzle of the toothpaste tube is held at an angle of 45° to the rack device. Pressure is applied at the bottom of the tube and a uniform ribbon of paste is squeezed from the tube. While the ribbon of paste is being extruded, the tube is moved across the rack in a straight line as fast as possible. There is no time limit fixed to stretch the ribbon of paste over the rack. If the ribbon breaks before the entire rack is traversed, the procedure is repeated. The ribbon is allowed to stand for 30 seconds and the rod number corresponding to where the ribbon breaks is recorded as the Cuban value. The test was performed four times and the average reading was recorded, rounding off to the nearest whole number. The test values are plotted in FIG. 3.

While this invention has been described in detail with reference to certain preferred embodiments, it should be appreciated that the present invention is not limited to those precise embodiments. Rather, in view of the present disclosure, many modifications and variations would present themselves to those skilled in the art without departing from the scope and spirit of this invention.

What is claimed is:

1. A substantially anhydrous thickener system in the form of a gel for use in oral care compositions comprising:
   (i) carboxymethyl cellulose, or a salt thereof, present in an amount from about 0.1% to about 2.0% of the thickener system;
   (ii) a chelating agent consisting of disodium pyrophosphate, present in an amount from about 0.01% to about 2.0% of the thickener system; and
   (iii) hydroxyethyl cellulose, present in an amount from about 0.1% to about 1.0% of the thickener system;
   (iv) a solvent or solvent system; and
   (v) water in an amount from about 0.1% to about 10% by weight of the solvent system,
   wherein the solvent system is first combined with the carboxymethyl cellulose or salt thereof, the hydroxyethyl cellulose, and the water heated to an elevated temperature ranging from about 70° C. to about 120° C. before the chelating agent is added at the elevated temperature to form a gel.

2. The thickener system according to claim 1, wherein the carboxymethyl cellulose or its salt has an average molecular weight range of 70,000 g/mol to 1,100,000 g/mol and an average degree of polymerization from 300 to 4,800.

3. The thickener system according to claim 1, wherein the hydroxyethyl cellulose has an average molecular weight ranging from about 90,000 g/mol to about 1,300,000 g/mol and an average degree of polymerization from about 300 to about 4,800.

4. The thickener system according to claim 1, wherein the solvent system is selected from a group consisting of glycerin, diglycerin, sorbitol, lactitol, xylitol, propylene glycol, polyethylene glycol, and combinations thereof.

5. The thickener system according to claim 1, wherein the solvent or solvent system is present in an amount from about 94% to about 99.7% by weight of the thickener system.

6. The substantially anhydrous thickener system of claim 1, wherein the solvent system comprises glycerin, propylene glycol, and polyethylene glycol.

7. The substantially anhydrous thickener system of claim 1, wherein the chelating agent comprises disodium pyrophosphate in an amount from about 0.01% to about 2% w/w; and the solvent system comprises glycerin, propylene glycol, and polyethylene glycol.

8. An oral care composition comprising:
   i) a substantially anhydrous thickener system in the form of a gel comprising:
      (a) carboxymethyl cellulose, or a salt thereof, present in an amount from about 0.1% to about 2.0% of the thickener system;
      (b) a chelating agent consisting of disodium pyrophosphate, present in an amount from about 0.01% to about 2.0% of the thickener system;
      (c) hydroxyethyl cellulose, present in an amount from about 0.1% to about 1.0% of the thickener system;
      (d) a solvent or solvent system; and
      (e) water in an amount from about 0.1% to about 10% by weight of the solvent system,
   wherein the solvent system is first combined with the carboxymethyl cellulose or salt thereof, the hydroxyethyl cellulose, and the water and heated to an elevated temperature ranging from about 70° C. to about 120° C. before the chelating agent is added at the elevated temperature to form a gel; and
   ii) one or more acceptable oral acceptable additives.

9. An oral care composition according to claim 8 comprising:
   (A) from about 50 to about 90% w/w of the substantially anhydrous thickener system; and
   (B) from about 10 to about 50% w/w of the one or more acceptable oral additives.

10. The oral care composition according to claim 8, wherein the orally acceptable additive is selected from the group consisting of pH adjusting agents and/or buffers, humectants, polishing agents, fluoride ion sources, flavoring agents, sweetening agents, surfactants, rheology modifying agents, antibacterial agents, anti-inflammatory agents, whitening agents, anti-caries agents, enamel repair agents, breath freshening agents, foaming agents, solubilizing agents, tartar control agents, anti-stain ingredients, anti-erosion ingredients, opacifying agents, enzymes, sensate ingredients, stabilizers, coloring agents, abrasive compounds, foaming agents and combinations thereof.

11. The oral care composition according to claim 9, wherein pH of the composition is from about 4 to about 9.

* * * * *